(12) United States Patent
Shoaf

(10) Patent No.: US 7,074,365 B1
(45) Date of Patent: Jul. 11, 2006

(54) DETECTOR FOR HALOGEN TOXICANTS AND METHOD

(76) Inventor: Antony R. Shoaf, 2386 Horseshoe Neck Rd., Lexington, NC (US) 27295

( * ) Notice: Subject to any disclaimer, the term of this patent is extended or adjusted under 35 U.S.C. 154(b) by 628 days.

(21) Appl. No.: 10/127,291

(22) Filed: Apr. 22, 2002

Related U.S. Application Data

(63) Continuation-in-part of application No. 10/035,277, filed on Nov. 19, 2001, now Pat. No. 6,815,178.

(51) Int. Cl.
*C12Q 1/68* (2006.01)
*G01N 15/06* (2006.01)
*G01N 33/00* (2006.01)
*G01N 33/48* (2006.01)
*B32B 5/02* (2006.01)

(52) U.S. Cl. .................. 422/82.08; 422/50; 422/52; 422/68.1; 422/82.05; 422/82.07; 422/83; 422/91; 436/124; 436/125; 436/126; 436/164; 436/172; 73/1.01; 73/1.02; 73/53.01

(58) Field of Classification Search .............. 422/50, 422/52, 68.1, 82.05, 82.07, 82.08, 83, 91; 436/124, 125, 126, 164, 172; 73/1.01, 1.02, 73/53.01
See application file for complete search history.

(56) References Cited

U.S. PATENT DOCUMENTS

| | | | | |
|---|---|---|---|---|
| 3,671,450 A | * | 6/1972 | Rauhut et al. | 252/700 |
| 4,193,963 A | * | 3/1980 | Bruening et al. | 422/52 |
| 4,665,022 A | * | 5/1987 | Schaeffer et al. | 435/7.72 |
| 5,173,264 A | * | 12/1992 | Zaromb et al. | 422/88 |
| 5,340,714 A | * | 8/1994 | Katsilometes | 435/6 |
| 5,792,621 A | * | 8/1998 | Verostko et al. | 435/14 |
| 5,837,195 A | * | 11/1998 | Malek et al. | 422/52 |
| 5,885,529 A | * | 3/1999 | Babson et al. | 422/65 |
| 6,087,183 A | * | 7/2000 | Zaromb | 436/178 |
| 6,406,667 B1 | * | 6/2002 | Singh et al. | 422/52 |
| 6,461,570 B1 | * | 10/2002 | Ishihara et al. | 422/65 |
| 6,485,962 B1 | * | 11/2002 | Tabacco et al. | 435/288.7 |
| 6,767,733 B1 | * | 7/2004 | Green | 435/288.5 |
| 6,803,238 B1 | * | 10/2004 | Eggers | 436/518 |

OTHER PUBLICATIONS

Article published in IEEE Engineering in Medicin;e and Biology, Sep./Oct. 2002 issue, Elizabeth D. Lester and Adrian Ponce, *An Anthrax "Smoke" Detector*, pp. 38-42.
Article on Elizabeth Lester found on www.jpl.nasa.gov web site, published Oct. 23, 2002, *College Student's Curiosity Leads to Discovery*, 2 pages.

(Continued)

*Primary Examiner*—Jill Warden
*Assistant Examiner*—Brian Sines

(57) ABSTRACT

The invention herein provides for the detection of certain organic halogen-containing agents or toxicants such as sarin, chloropicrin, mustard gas, mustard chlorohydrin, phosgene, chlorine, soman, lewisite, diphosgene and others by, in one embodiment, first reacting the agents with superoxide free radical anion ($.O_2^-$) to produce light pulses which can be detected by a standard photon counter. The superoxide may be available from a dimethyl sulfoxide superoxide ($.O_2^-$) liquid solution, from lecithin coated beads charged with superoxide ($.O_2^-$) in a reaction vessel or from a quarternary ammonium ion exchange resin charged with superoxide anion ($.O_2^-$) in a reaction vessel.

13 Claims, 4 Drawing Sheets

OTHER PUBLICATIONS

Article found on www.jpl.nasa.gov web site, published Oct. 23, 2002, *NASA Develop Biohazard "Smoke" Detector*, 2 pages.

Article found on www.nasatech.com web site, published under the NASA Tech Briefs, Jan. 2003, *NASA Biohazard Monitor Mimics a Smoke Detector*, 1 page.

Chemiluminescence Emission during Reactions between Superoxide and Selected Aliphatic and Aromatic Halocarbons in Aprotic Media; Antony R. Shoaf, Ali U. Shaikh, Joseph H. Ford, William C. Carlson and Richard H. Steele; Copyright 1996 by John Wiley & Sons, Ltd; J Biolumin Chemilumin 1996; 11: pp. 9-22; seven (7) pages front and back.

Extraction and Analysis of Superoxide Free Radicals ($\cdot O_2^-$) from Whole Mammalian Liver; Antony R. Shoaf, Ali U. Shaikh, Raymond D. Harbison and Ocsar Hinojosa; Copyright 1991 by John Wiley & Sons, Ltd.; Journal of Bioluminescence and Chemiluminescence vol. 6, pp. 87-96 (1191); ten (10) pages.

Welcome to HKUST Calcium-Aequorin Imaging Laboratory, Biology, Hong Kong University of Science & Technology; Image Photon Detectors and Data Acquisition stations; three (3) pages; last updated Oct.18, 2001.

Science Wares; Photon Imaging System Description; Copyright 2000 Science Wares; five (5) pages; last updated Oct. 27, 2000.

Science Wares; Calcium Imaging Publications; Copyright 1998 Science Wares; one (1) page; last updated Mar. 18, 1998.

Chelation Characteristics of Calcium in Relation to Water Binding and Heat Resistance of Bacterial Endospores; K. S. Rahan and N. Grecz; Spong Research 1997, vol. 2; pp. 527-543; seventeen (17) pages.

Effect of calcium chelators on the $Ca^{2+}$-dependent luminescence of aequorin; Osamu Shimomura and Akemi Shimomura; Biochem. J. (1984) 221; 907-910; four (4) pages.

* cited by examiner

DETECTOR FOR HALOGEN TOXICANTS AND METHOD

This is a continuation-in-part of patent application Ser. No. 10/035,277, filed 19 Nov. 2001, now U.S. Pat. No. 6,815,178.

FIELD OF THE INVENTION

The invention herein pertains to detection devices and methods, and particularly pertains to the detection by chemiluminescence of halogen-containing gaseous toxicants as used in chemical warfare agents or as found in environmental pollutants.

DESCRIPTION OF THE PRIOR ART AND OBJECTIVES OF THE INVENTION

Certain halogen-containing organic compounds will cause luminescence when reacted with superoxide free radical anion ($.O_2^-$). The luminescence is caused by the photon emission of excited singlet molecular oxygen which is generated in the reaction. The luminescence is detected by a photon counter, as described below.

$$RX + .O_2^- \rightarrow {}^1O_2^* + R + X^-$$

$$^1O_2^* \rightarrow {}^3O_2 + h\checkmark_{Cl}$$

Where:
RX=halogen-containing organic compounds
$h\checkmark_{Cl}$=photon emission (chemiluminescence)
halogens (X)=fluorine, chlorine, bromine, iodine
$^1O_2^*$=excited singlet molecular oxygen
$^3O_2$=ground state triplet molecular oxygen An emission of photons can be detected and measured by a conventional liquid scintillator spectrometer as described in my earlier pending patent application entitled Endospore Detector And Method, Ser. No. 10/035,277 filed 19 Nov. 2001, now U.S. Pat. No. 6,815,178, the details of which are incorporated herein by reference.

Chemical warfare agents such as sarin, chloropicrin, mustard gas, mustard chlorohydrin, phosgene, chlorine, soman, lewisite and diphosgene contain halogens and are used to injure, attack and kill enemy soldiers. Terrorists can also use these warfare agents against civilian populations. Halogens are fluorine, chlorine, bromine and iodine.

Liquid scintillation spectrometers are commonly used to measure radioisotopes in medical research. These same instruments, when used in an out-of-coincidence mode at an ambient temperature of 22° C., may also be used as a photon (light pulse) counter to measure luminescence of chemical or reactions.

While various types of detection methods for certain deadly endospores such as *bacillus anthracis* (anthrax) and halogen-containing organic warfare agents and toxicants are known, these methods generally consist of collecting specimens from office buildings, homes, battlefields or the like and thereafter delivering them to a laboratory for analysis. While such laboratory analyses may be very accurate, they are time consuming in that the collection, delivery and analytical work can take valuable time. Thus, those unfortunate enough to be attacked or assaulted may be diagnosed and treated too late to prevent bodily injury and/or to save their lives.

Therefore, in view of the need for a speedy and continuous method of detecting deadly halogen-containing toxicants in buildings, battlefields and other locales the present invention was conceived and one of its objectives is to provide a device and method whereby such toxicants can be easily, quickly and inexpensively detected.

It is also an objective of the invention to provide a device and method for accurately detecting certain halogen-containing organic agents or toxicants used as weapons or when occurring accidentally, as through inadvertent leaking of a container.

It is another objective of the present invention to provide a device and method for detecting certain halogen-containing toxicants which is relatively simple to operate and requires little specialized training.

It is yet another objective of the present invention to provide a method for detecting halogen-containing toxicants which is relatively inexpensive to operate continuously twenty-four hours a day.

It is still another objective of the present invention to provide a method of detecting halogen-containing toxicants utilizing an anhydrous DMSO (dimethyl sulfoxide) liquid in a reaction vessel of a scintillation spectrometer.

It is yet another objective of the present invention to provide a method for detecting halogen-contaminating toxicants utilizing certain quaternary ammonium agents such as phosphatidyl choline, coated on glass beads.

It is still another objective of the present invention to provide an alternative method of detection of halogen-containing toxicants utilizing phosphatidyl choline-containing glass beads charged with superoxide free radical anion ($.O_2^-$) in a reaction vessel of a scintillation spectrometer.

It is yet another objective of the present invention to provide a method for detecting halogen-containing toxicants utilizing certain quaternary ammonium agents such as beaded ion exchange resins composed of a styrene and divinyl benzene copolymer covalently bound to trimethyl benzyl ammonium cations.

It is yet another objective of the present invention to provide an alternative method of detection of halogen-containing toxicants utilizing trimethyl benzyl ammonium-containing polystyrene ion exchange resin beads charged with fixed superoxide radical anions ($.O_2^-$) in a reaction vessel of a scintillation spectrometer.

It is yet another objective of the present invention to provide a method for detecting various harmful halogen-containing environmental pollutants, such as carbon tetrachloride, methylene chloride, chloroform, ethylene dibromide, dioxin, polychlorinated biphenyls, polybrominated biphenyls and others, utilizing the procedures described above.

Various other objectives and advantages of the present invention will become apparent to those skilled in the art as a more detailed description is set forth below.

SUMMARY OF THE INVENTION

The aforesaid and other objectives are realized by providing a scintillation spectrometer with a reaction vessel containing, in the preferred embodiment, a chemiluminescent liquid. The reaction vessel is joined to an air pump by an intake conduit. The air pump delivers air from a building, room, battlefield or the like through a hydrophobic membrane filter capable of excluding moisture and on into the reaction vessel holding the chemiluminescent liquid. Halogen-containing agents or toxicants such as sarin, chloropicrin, mustard gas, mustard chlorohydrin, phosgene, chlorine, soman, lewisite and diphosgene will then react with the chemiluminescent liquid which provides the singlet molecular oxygen ($^1O_2^*$) to produce chemiluminescence. This chemiluminescent reaction emits photons of light which are directed through the walls of the glass reaction vessel, through a light guide and into photomultiplier tubes where they are intensified. Analog signals resulting therefrom are then delivered to a ratemeter which in turn delivers corresponding electrical signals to a chart recorder and, if desired, to a printer or personal computer.

In a second embodiment of the invention a chemiluminescent solid in the form of glass beads are employed that have been coated with a choline containing lecithin charged with superoxide free radical anion (.$O_2^-$) to produce chemiluminescence.

In a third embodiment of the invention a chemiluminescent solid in the form of resinous ion exchange beads are employed that have been coated with quaternary ammonium cations (e.g. trimethylbenzyl ammonium being preferred) charged with superoxide free radical anion (.$O_2^-$) to produce chemiluminescence.

In another embodiment of the invention the scintillation spectrometer converts light pulses to digital signals which are sent to a personal computer (PC) whereby the signals can be read in real time on the PC monitor. A halogen-containing agent or toxicant is pumped to chemiluminescence liquid, glass beads or polystyrene resin beads, thereby producing a chemiluminescent reaction for detection as described above.

DETAILED DESCRIPTION OF THE PREFERRED EMBODIMENTS AND OPERATION OF THE INVENTION

Figure 1:
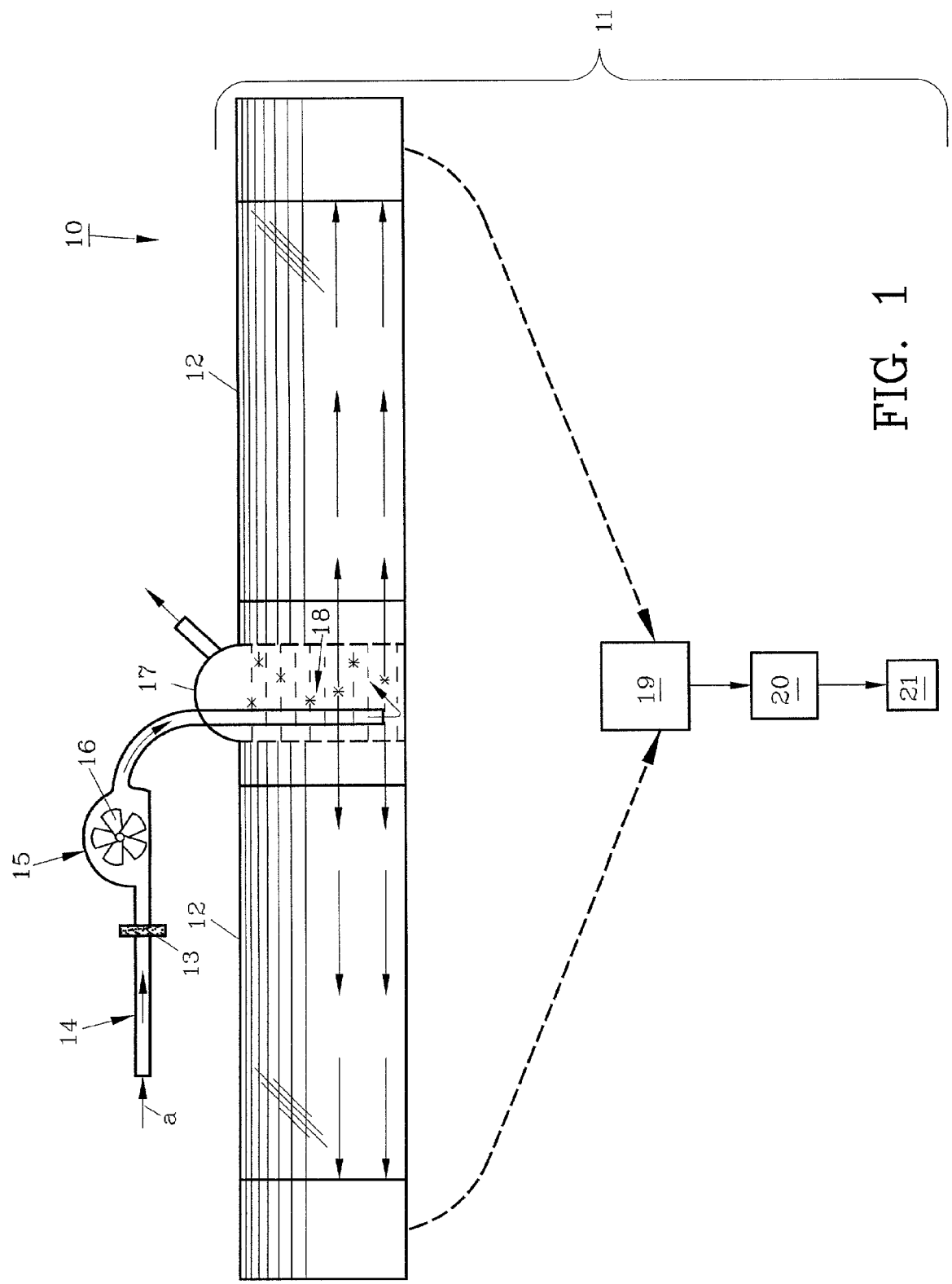
FIG. 1 shows a schematic representation of the preferred detection device of the invention using a liquid phase chemiluminescent reaction.

For detection of halogen-containing warfare toxicants such as sarin (methylphosphonofluroidic acid 1-methylethyl ester);

chloropicrin (trichloronitromethane);

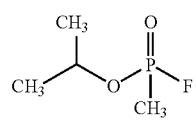

mustard gas (1,1'-thiobis[2-chloroethane]);

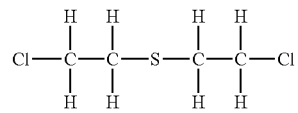

mustard chlorohydrin (2-(2-chlorcethylthio)ethanol);

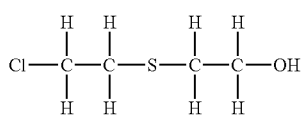

phosgene (carbonic dichloride);

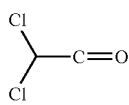

chlorine (chlorine gas);

Cl—Cl soman (methylphosphonofluoridic acid 1,2,2-trimethylpropyl ester);

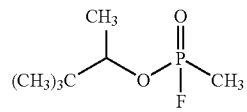

lewisite ((2-chloroethenyl)arsonous dichloride);

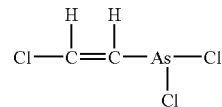

and diphosgene (carbonochloridic acid trichloromethyl ester);

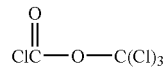

the preferred method is demonstrated in FIG. 1 whereby air having halogen-containing warfare agents or toxicants is represented by arrow 'a'. Preferred device 10 for detecting such agents is shown in schematic fashion utilizing a model 3320 Packard Liquid Scintillation spectrometer 11 as sold by Packard Instrument Company of Downers Grove, Ill. operated in an out-of-coincidence mode at the preferred ambient temperature of 22° C. Device 10 is used for continuous monitoring of analog signals received from each of the photomultiplier tubes 12, 12'.

As seen, halogen-containing warfare agents are first directed through hydrophobic membrane filter 13 (capable of removing moisture) of air tube 14 by air pump 15 which then forces the dry air through intake conduit 16 and on into reaction vessel 17. Conventional hydrophobic membrane 13 is a standard molecular sieve for removing moisture from passing gases.

As also shown in FIG. 1, reaction vessel 17 contains a chemiluminescent substance, preferably chemiluminescent liquid 18 comprising:

- Dimethyl sulfoxide (DMSO) (as purchased from Sigma Chemical Co.) is made anhydrous by passing a 200 ml aliquot over a bed of basic alumina (column width: 2.5 cm; column height: 30 cm).
- Sufficient tetrabutylammonium perchlorate (TBAP) is added to 100 ml of anhydrous DMSO to yield a 0.1 mol/L solution of TBAP in DMSO.
- The DMSO/TBAP solution is further rendered anhydrous by purging for twenty minutes with dry argon gas.
- Potassium superoxide in DMSO/TBAP is prepared as follows: to a 250-ml glass stoppered Ehrlenmeyer flask is added 100 ml of argon purged anhydrous DMSO/TBAP solution. To the flask is then added about 5 grams of solid potassium superoxide (Alfa Ventron Chemicals, $KO_2$) crystals. The crystals will settle to the bottom of the flask. After about thirty minutes a saturated solution of $KO_2$ in DMSO/TBAP will be obtained. The $KO_2$ concentration is 5.5 mmol/L. This is chemiluminescent liquid 18.
- 20 ml of chemiluminescent liquid 18 containing 0.1 mol/L tetrabutyl ammonium perchlorate (TBAP), 5.5 mmol/L superoxide free radical anion ($.O_2^-$) in DMSO is added to reaction vessel 17.

Chemiluminescent liquid 18 as thus prepared is then placed in reaction vessel 17 as manufactured by Fisher Scientific of Pittsburgh, Pa. 15275, preferably made of quartz, though borosilicate low potassium glass may also be used. Reaction vessel 17 preferably has a height of 61 mm and an outside diameter of 28 mm. Standard air pump 15 as shown preferably provides a 5.0 L/min gas flow rate to reaction vessel 17 through Teflon (trademark of E.I. DuPont DeNemours and Co., Wilmington, Del.), intake conduit 16 which has a diameter of 4 mm. As would be further understood from FIG. 1, light pulses from reaction vessel 17 are directed through photomultiplier tubes 12, 12' and are directed to ratemeter 19, preferably model 280A as manufactured by Packard Instrument Company. The light pulses generated in reaction vessel 17 are a result of the chemical reactions shown below:

$$RX + .O_2^- \rightarrow R. + X^- + {}^1O_2^*$$

$$^1O_2^* \rightarrow {}^3O_2 + h\nu_{Cl}$$

Where:
RX=halogen-containing warfare agent (toxicant)
$^1O_2^*$=singlet molecular oxygen
$.O_2^-$=superoxide free radical anion
$h\nu_{Cl}$=photons of light
$^3O_2$=ground state oxygen Light pulses from the chemical reaction are directed from reaction vessel 17 through photomultiplier tubes 12 and on to ratemeter 19 as seen in FIG. 1. Signals are sent from ratemeter 19 as illustrated schematically in FIG. 1 to standard Honeywell Electronik strip chart recorder 20 and on to standard Monroe digital printer 21. Separate count per minute readings can be then printed as desired. While a model 3320 Packard Instrument liquid scintillation spectrometer is preferred, various other types of spectrometers could likewise be used.

Standard scintillation spectrometer 11 as seen in FIG. 1 includes photomultiplier tubes 12, 12' which are preferably manufactured by EMI Thorn Company (now Electron Tube Company), (England) as catalogue No. 9635QB. Tubes 12, 12' are sensitive to the wavelengths of light corresponding to the maximum wavelength of light emissions produced by excited singlet molecular oxygen ($^1O_2^*$).

Figure 2:
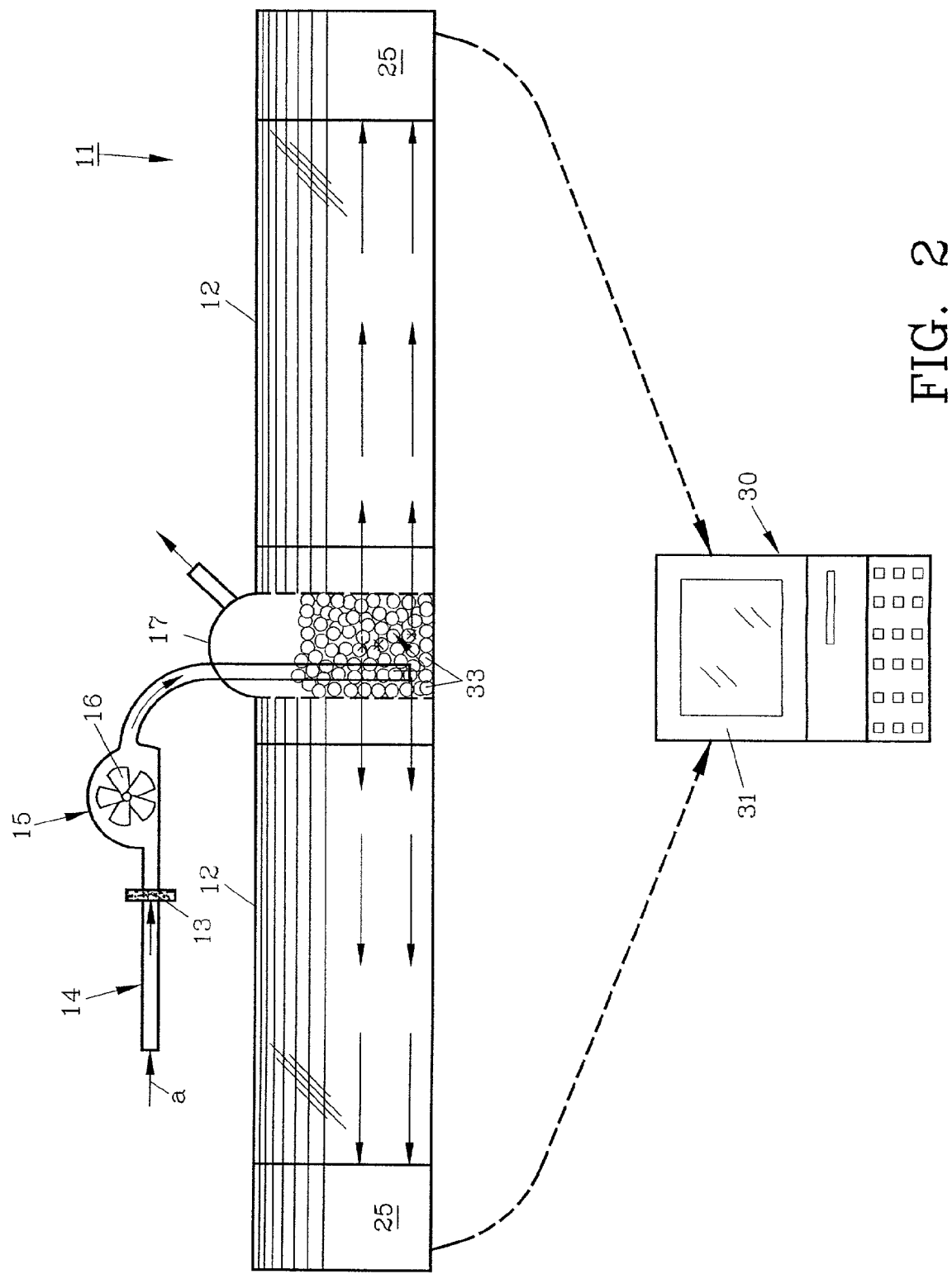
FIG. 2 demonstrates schematically an alternate embodiment of the invention as shown in FIG. 1 utilizing a gaseous phase chemiluminescent reaction.
Figure 3:
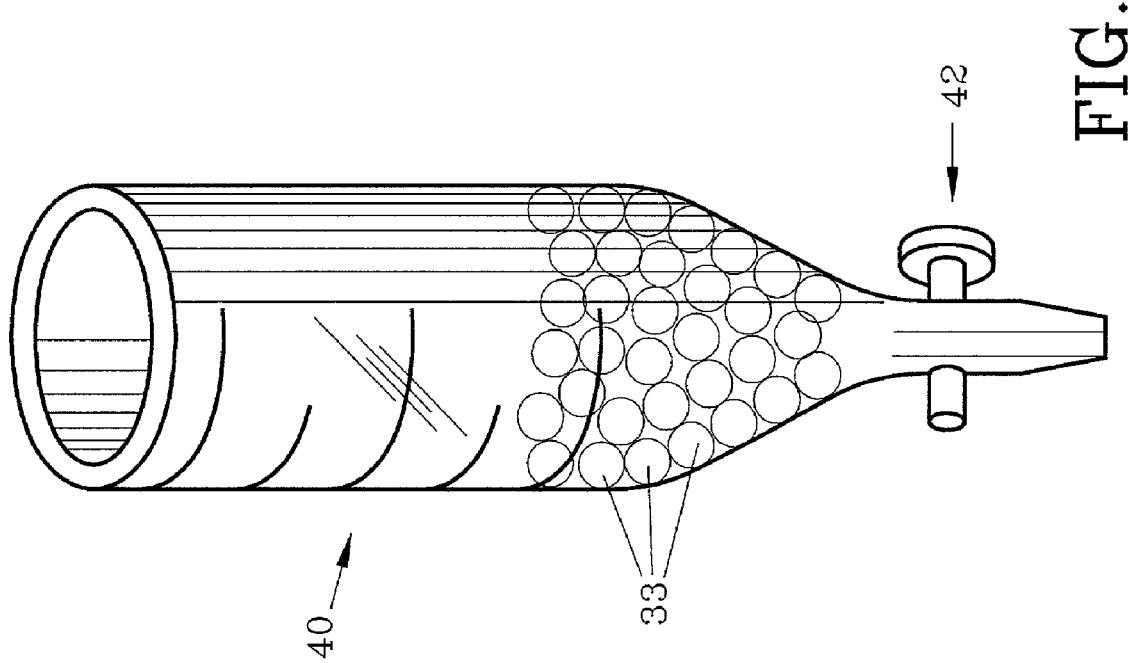
FIG. 3 illustrates a glass burette containing glass beads.

In an alternate embodiment, a chemiluminescent solid substance is employed, namely lecithin coated glass beads 33 (although other lecithin supports may be used) in reaction vessel 17 as shown in FIG. 2, in place of scintillation liquid 18. Glass beads 33 which have been coated with lecithin-containing choline (see U.S. Pat. Nos. 4,931,498, 4,927,879) are preferably prepared as follows:

In a 250 ml dispensing burette, 20 ml of lecithin-coated beads are placed. 200 ml of anhydrous DMSO solution (prepared by passage over bed of basic alumina) which has been saturated with potassium superoxide ($KO_2$) is added. The DMSO solution is then allowed to drain through the burette leaving the moist beads 33, charged with $.O_2^-$. Next, a stream of water-free argon gas is directed onto moist beads 33 which then exits the burette stopcock 42 (see FIG. 3).

Figure 4:
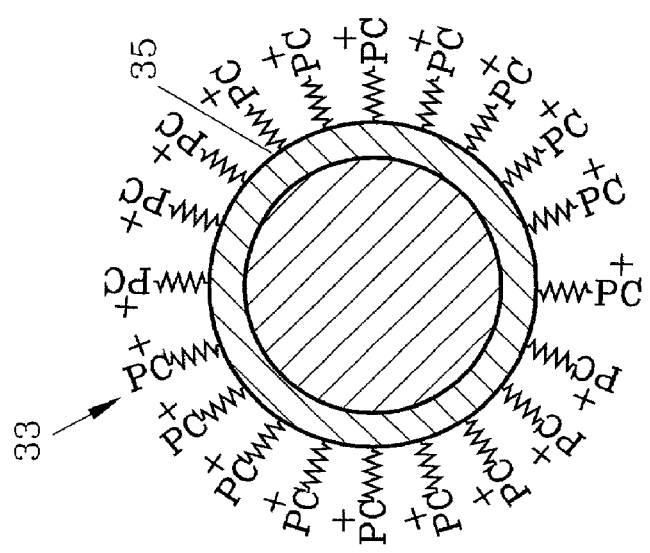
FIG. 4 depicts an enlarged schematic view of a phosphatidyl choline (lecithin) coated glass bead charged with a superoxide free radical anion (.$O_2^-$)
Figure 5:
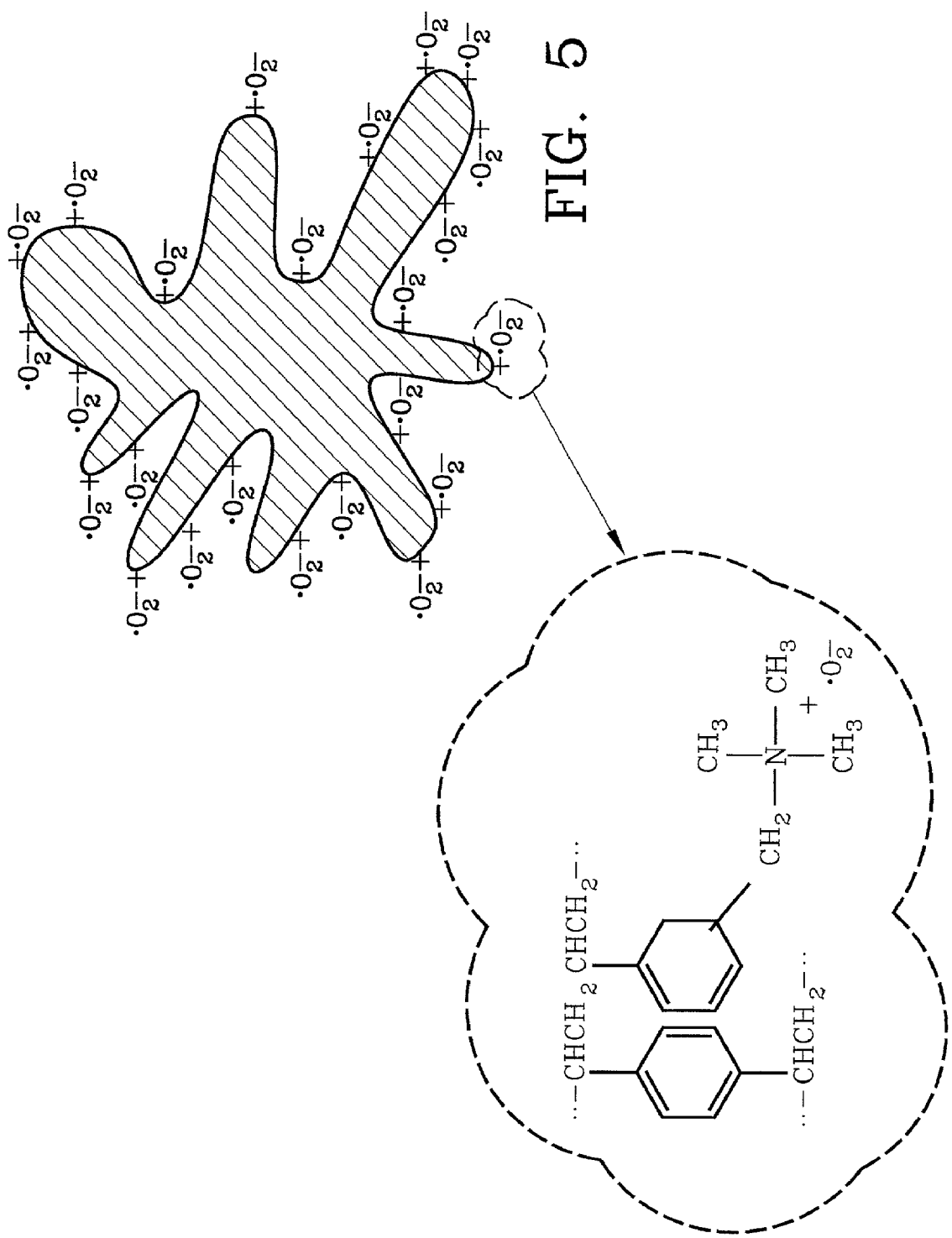
FIG. 5 features an enlarged cross-sectional view of an ion exchange resin bead bound to quaternary ammonium cations and charged with superoxide free radical anion (.$O_2$).

The dried $.O_2^-$-charged beads 33 (see FIG. 4) (generally 20 ml) are then placed in reaction vessel 17. Halogen-containing gases can then be passed therethrough for reaction purposes. Gas flow rates are between 5 L/min and 12 L/min.

In an alternate embodiment, a chemiluminescent solid substance is employed, namely trimethylbenzyl ammonium cation-coated polystyrene resin beads are placed in reaction vessel 17 as shown in FIG. 2, in place of scintillator liquid 18. Resin beads 34 which contain quaternary ammonium ions (commercially available from Sigma Chemical Company, St. Louis, Mo.) are preferably prepared as follows:

In a 250 ml dispensing burette, 20 ml of dry polystyrene resin is placed. 200 ml of anhydrous DMSO solution (prepared by passage over bed of basic alumina) which has been saturated with potassium superoxide ($KO_2$) is added. The DMSO solution is then allowed to drain through the burette leaving moist resin 34 charged with $.O_2^-$. Next, a stream of water-free argon gas is directed onto moist resin 34 which then exits burette stopcock 42 (see FIG. 3).

Dried $.O_2^-$-charged resin 34 (see FIG. 4) (preferably 20 ml) is then placed in reaction vessel 17. Halogen-containing gases or toxicants can then be passed therethrough for reaction purposes. Gas flow rates are between 5 L/min and 12 L/min.

In an alternate embodiment of the spectrometer as shown in FIG. 2, Packard liquid scintillation spectrometer 11 has been modified as schematically shown in FIG. 2 whereby its analog to digital convertor 25 is utilized and the resulting digital signal is fed to PC 30. PC monitor 31 can then be used for continuously monitoring the activity of reaction vessel 17 in real time.

While the preferred detection device 10 as shown in FIG. 1 is suitable for use as a table or desktop setup, device 10 could also be made portable and carried by a person. In this event the device would be miniaturized to some degree and have its own power source such as conventional batteries. A miniaturized version (not seen) may have dimensions of about 60 cm by 30 cm by 30 cm for portability.

The illustrations and examples provided herein are for explanatory purposes and are not intended to limit the scope of the appended claims.

I claim:

1. A device for detecting halogen-containing toxicants comprising: a reaction vessel, a chemiluminescent substance, said chemiluminescent substance comprising choline-containing beads charged with a superoxide free radical anion, said chemiluminescent substance contained within said reaction vessel, a spectrometer, said spectrometer positioned proximate said reaction vessel whereby halogen-containing toxicants directed into said reaction vessel will react with said chemiluminescent substance for detection by said spectrometer.

2. The device of claim 1 wherein said reaction vessel comprises a glass container.

3. The device of claim 1 wherein said chemiluminescent substance further comprises a DMSO solution.

4. The device of claim 3 wherein said DMSO solution further comprises potassium superoxide.

5. A device for detecting halogen-containing toxicants comprising: a reaction vessel, a chemiluminescent substance, said chemiluminescent substance comprising lecithin-coated beads charged with $.O_2^-$, said chemiluminescent substance contained within said reaction vessel, a spectrometer, said spectrometer positioned proximate said reaction vessel whereby halogen-containing toxicants directed into said reaction vessel will react with said chemiluminescent substance for detection by said spectrometer.

6. The device of claim 1 wherein said spectrometer comprises a liquid scintillation spectrometer.

7. A device for detecting halogen-containing toxicants comprising: a reaction vessel, a chemiluminescent substance, said chemiluminescent substance comprises a quaternary ammonium ion exchange resin charged with $.O_2^-$, said chemiluminescent substance contained within said reaction vessel, a spectrometer, said spectrometer positioned proximate said reaction vessel whereby halogen-containing toxicants directed into said reaction vessel will react with said chemiluminescent substance for detection by said spectrometer.

8. The device of claim 1 wherein said spectrometer comprises a pair of photomultiplier tubes.

9. The device of claim 1 further comprising an air pump, an air intake conduit, said air pump connected to said air intake conduit, said intake conduit in communication with said reaction vessel.

10. The device of claim 9 wherein said intake conduit has a diameter of 4 mm.

11. The device of claim 9 wherein said air pump forces air through said intake conduit at approximately 5 L/min. for liquid phase reactions and 5–12 L/min for gas phase reactions.

12. The device of claim 7 wherein said quaternary ammonium ion exchange resin comprises a styrene copolymer.

13. The device of claim 7 wherein said quaternary ammonium ion exchange resin comprises a divinyl benzene copolymer.

* * * * *